US00PP10070P

United States Patent [19]

Carruth

[11] Patent Number: Plant 10,070

[45] Date of Patent: Oct. 21, 1997

[54] SHRUB ROSE PLANT VARIETY NAMED 'WEKBOROCO'

[75] Inventor: Thomas F. Carruth, Altadena, Calif.

[73] Assignee: Weeks Wholesale Rose Grower, Inc., Upland, Calif.

[21] Appl. No.: 656,452

[22] Filed: May 31, 1996

[51] Int. Cl.[6] ..... A01H 5/00

[52] U.S. Cl. ..... Plt./1

[58] Field of Search ..... Plt./1, 11, 12, Plt./13, 22

*Primary Examiner*—Howard J. Locker

*Attorney, Agent, or Firm*—Christie, Parker & Hale, LLP

[57] ABSTRACT

A new variety of Shrub rose suitable for garden decoration, having flowers of striped red, pink and white coloration.

1 Drawing Sheet

BACKGROUND OF THE INVENTION

This invention relates to a new and distinct variety of Shrub Rose. The varietal denomination of the new variety is 'Wekboroco'. The plant is a bushy, slightly spreading and suitable for outdoor garden decoration. It has as its seed parent the variety known as 'Meidomonac' (U.S. Plant Pat. No. 5,105) and as its pollen parent the variety known as 'Macminmo' (U.S. Plant Pat. No. 7,319).

SUMMARY OF THE INVENTION

Among the features which distinguish the new variety from other presently available and known commercial rose cultivars are the following combination of characteristics: its striped upper petal surface with solid colored petal underside, its peduncles that are blushed a darker coloration and its elongated flower clusters. 'Wekboroco' may be asexually propagated by cuttings, budding, or grafting.

Asexual reproduction of the new variety by budding and own-root propagation as performed in Kern County and Upland, Calif. shows that the foregoing and other distinguishing characteristics come true to form and are established and transmitted through succeeding propagations.

Comparison with Parents

The new variety may be distinguished from its seed parent 'Meidomonac' (U.S. Plant Pat. No. 5,105) by the following combination of characteristics: whereas the seed parent produces flowers of a pure pink coloration, 'Wekboroco' produces flowers of a striped pink, red and white coloration. 'Meidomonac' produces very double flowers with over 40 petals, whereas the new variety produces flowers with significantly fewer petals (about 33 to 37).

The new variety may be distinguished from its pollen parent, 'Macminmo' (U.S. Plant Pat. No. 7,319), by the following combination of characteristics: whereas the pollen parent bears single petaled flowers, 'Wekboroco' bears flowers of significantly higher petalage (about 33 to 37). 'Macminmo' has long canes and produces a more spreading plant habit, whereas the new seedling has significantly shorter canes with a more rounded plant habit.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of specimens of the new cultivar grown outdoors in Upland, Calif. in the month of October. Phenotypic expression may vary with environmental, cultural and climatic conditions, as well as differences in conditions of light and soil.

Flower

The new variety bears its flowers usually in clusters of five or more per stem. Flowers are borne in regular rounded to pyramidal clusters on normal caliper long stems (about 40 to about 50 cm.) for the class. Outdoors the plant blooms very freely and nearly continuously during the growing season. The flowers have a slight apple-like fragrance.

Bud

The peduncle is of short length for the class (about 2.4 to about 3.3 cm.), of average caliper and usually erect. It is moderately rough, with many stipitate glands. Peduncle color is between 144A and 137B , often moderately suffused with between 166A and 183A.

Before the calyx breaks, the bud is small in size for the class (about 1.1 to about 1.6 cm. in diameter at the widest point), short in length (about 1.0 to about 1.5 cm.), and pointed to globular in shape. The surface of the bud bears some stipitate glands and few hairs, usually with slender entire foliaceous parts extending beyond the tip of the bud equal to ½ or more of its length. Bud color is between 144A and 137B, often lightly suffused with between 166A and 183A on the side facing the sun.

The inner surface of the sepals is covered with fine wooly tomentum; sepal margins are lined with some stipitate glands.

As the petals open, the bud is moderately small for the class (about 1.4 to about 1.8 cm. in diameter at the widest point), moderately short in length (about 1.2 to about 1.8 cm.), and pointed to globular in shape. The color of the under surfaces of the newly opened petals is between 155B and 155D, often blushed on the side exposed to the sun with as deep as near 53A. The color of the upper surfaces of the newly opened petals is irregularly striped with as light as between 155B and 155D or as dark as between 53A and 46A. At the point where the petal attaches, there is a moderately large zone of between 155B and 4D. The bud opens up well and is generally not prevented from opening by wet, cold, hot or dry weather.

Bloom

When fully open, the bloom is small to medium sized for the class, ranging from about 5 to about 7 cm. in diameter. Petalage is very double with about 33 to 37 petals and about 4 to 9 petaloids arranged regularly. When partially open, the bloom form is moderately cupped to globular, and the petals are somewhat tightly spiraled to cupped with petal edges somewhat rolled outward. When fully open, the bloom form is cupped to globular, and the petals are more loosely cupped to undulated with petal edges somewhat rolled outward.

Petals

The substance of the petals is moderately heavy and of medium thickness, with upper surfaces somewhat satiny to velvety and under surfaces moderately shiny. The outer petals are somewhat round to broadly obovate in shape with apices moderately rounded to sometimes mucronate. The intermediate petals are more obovate in shape with rounded apices. The inner petals are more narrowly obovate to oblanceolate in shape with rounded apices.

Newly Opened Flower

The under surface of the outer, intermediate and inner petals is between 155B and 155D.

The upper surface of the outer petals is irregularly striped with as light as between 155B and 155D or as dark as between 53A and 46A. The white portion of the petals which has been exposed to the sun is often blushed with between 55B and 53D. At the point where the petal attaches, there is a moderately large zone of between 155B and 155D.

The upper surface of the intermediate and inner petals is of similar coloration but with little blushing of color on the white portion.

The general tonality of the newly opened flower is irregularly striped with as light as between 155B and 155D or as dark as between 53A and 46A.

Three Day Old Flower

The under surface of the outer and inner petals is between 155B and 155D.

The upper surface of the outer and inner petals is irregularly striped with as dark as between 53B and 46A or as light as between 155B and 155D. The white portion of the petal which has been exposed to the sun is often blushed with between 62A and 53D. At the point where the petal attaches, there is a moderately large zone of between 155B and 155D.

The general tonality of the three day old flower is irregularly striped with as dark as between 53B and 46A or as light as between 155B and 155D.

On the spent bloom, the petals usually drop off cleanly.

In October, blooms on the bush growing outdoors generally last from four to five days. Cut roses grown outdoors and kept at normal indoor living temperatures generally last from four to five or more days.

Male Reproductive Organs

Stamens are few in number and are arranged regularly about the pistil. The filaments are of irregular to moderately short lengths, most with anthers. The anthers are moderately small for the class and all open approximately at the same time. Anther color is near 14D when immature and near 163C at maturity. Pollen is somewhat sparse and near 11C in color.

Female Reproductive Organs

Pistils vary in number (approximately 60). The styles are somewhat uneven, moderately long in length, thin in caliper, and loosely bunched. Stigma and style color is near 1C. Ovaries are usually all enclosed in the calyx.

Hips have not been observed on this variety when grown in Upland, Calif.

Foliage

The compound leaves are usually comprised of three to five or more leaflets and are borne abundantly. The leaves are moderately small for the class (about 6.0 to about 9.5 cm. in length and about 5.5 to about 7.0 cm. in width at the widest point), moderately heavy to leathery in texture, and glossy to semi-glossy in finish. The leaflets are moderately small for the class (about 2.8 to about 4.2 cm. in length and about 1.8 to about 2.4 cm. in width at the widest point), oval in shape with acute apices and acute bases. Their margins are usually serrate.

The upper surface of the mature leaf is between 137A and 136B. The under surface of the mature leaf is between 147B and 191A. The upper surface of the young leaf is between 137A and 136B, sometimes lightly suffused, especially at the leaf margin, with between 183A and 187B. The under surface of the young leaf is between 137C and 136C, sometimes lightly suffused with between 183B and 187B.

The rachis is somewhat light to average in caliper and somewhat rough. The upper side is shallowly grooved with many hairs and some stipitate glands on the edges. The under side of the rachis is somewhat rough with many hairs and some stipitate glands.

The stipules are of medium to long length with moderately wide medium length straight points that usually turn out at an angle of more than 45 degrees.

The plant displays an above average degree of resistance to powdery mildew, rust and downy mildew as compared to other commercial varieties grown under comparable conditions in Upland, Calif.

Growth

The plant has a bushy slightly spreading to sprawling medium height (about 130 to about 160 cm. in height and about 120 to about 140 cm. spread at the widest point), with very full branching. It displays very vigorous growth and the canes are of light to medium caliper for the class.

The color of the major stems is near 146D. They bear several large prickles which are of medium length for the class (about 0.8 to about 1.1 cm.). The large prickles are almost straight angled slightly downward with a moderately short nearly rounded to broadly oval base; prickle color is near 164A.

The color of the branches is between 144A and 139B. They bear several large prickles which are of similar shape and size to the large prickles on the major stems; prickle color is near 162B.

The color of the new shoots is between 144B and 139B sometimes lightly suffused with near 183B. They bear several large prickles which are of similar shape and size to the large prickles on the major stems; prickle color is near 160C often moderately suffused with near 183B.

I claim:

1. A new and distinct variety of shrub rose plant substantially as herein described and illustrated.

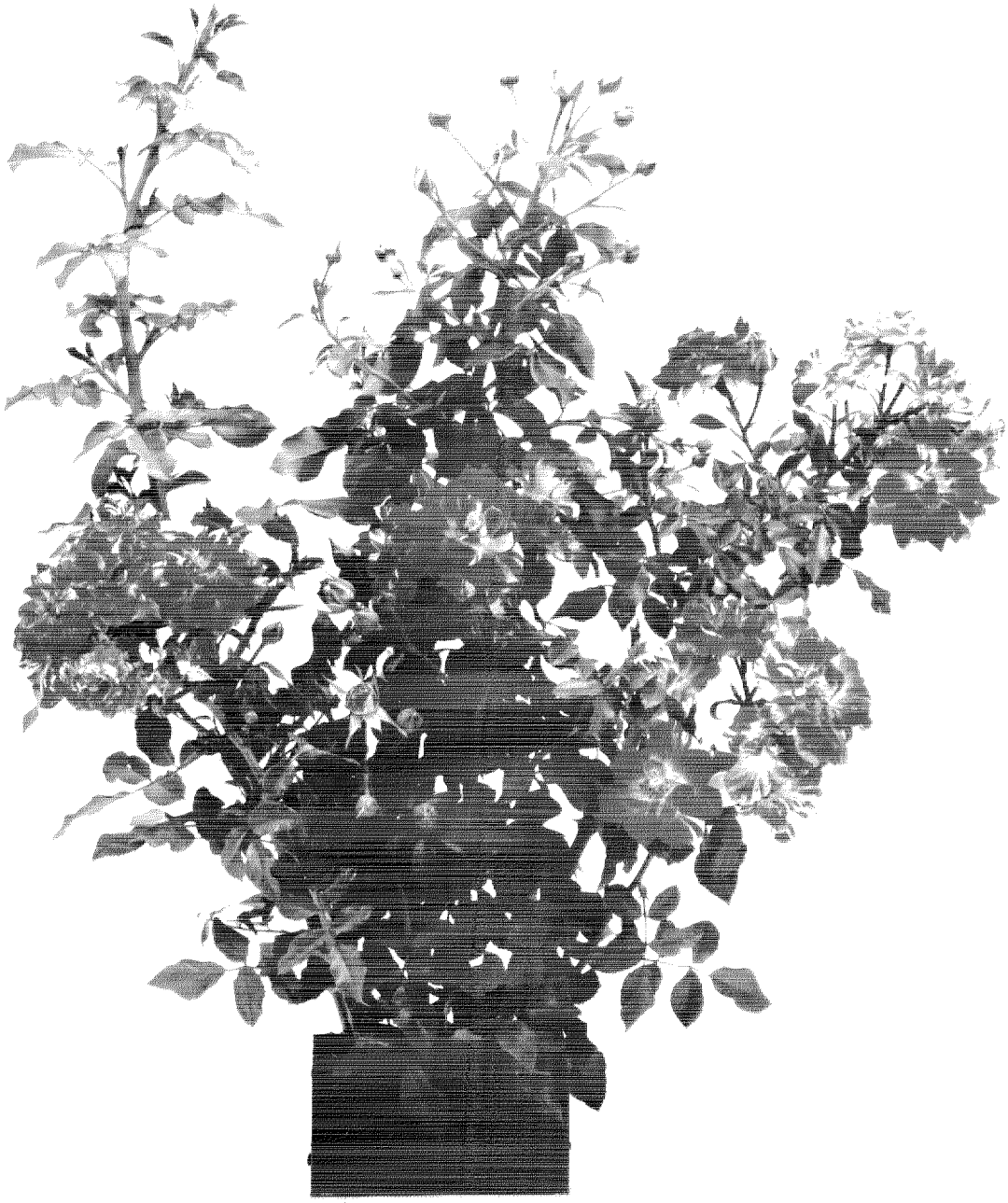

* * * * *